United States Patent
McDonald

(10) Patent No.: US 11,419,712 B2
(45) Date of Patent: Aug. 23, 2022

(54) ENDOLUMINAL DEVICE

(71) Applicant: VASCUTEK LIMITED, Renfrewshire (GB)

(72) Inventor: Gary McDonald, Strathclyde (GB)

(73) Assignee: Vascutek Limited, Renfrewshire (GB)

( * ) Notice: Subject to any disclaimer, the term of this patent is extended or adjusted under 35 U.S.C. 154(b) by 0 days.

(21) Appl. No.: 16/641,591

(22) PCT Filed: Sep. 26, 2018

(86) PCT No.: PCT/GB2018/052742
§ 371 (c)(1),
(2) Date: Feb. 24, 2020

(87) PCT Pub. No.: WO2019/063998
PCT Pub. Date: Apr. 4, 2019

(65) Prior Publication Data
US 2020/0214821 A1 Jul. 9, 2020

(30) Foreign Application Priority Data
Sep. 27, 2017 (GB) ..................... 1715658

(51) Int. Cl.
*A61F 2/04* (2013.01)
*A61F 2/95* (2013.01)
*A61F 2/06* (2013.01)

(52) U.S. Cl.
CPC .............. *A61F 2/04* (2013.01); *A61F 2/9517* (2020.05); *A61F 2002/045* (2013.01); *A61F 2002/065* (2013.01); *A61F 2250/0013* (2013.01)

(58) Field of Classification Search
CPC .......... A61F 2/04; A61F 2/954; A61F 2/2475; A61F 2250/0039
(Continued)

(56) References Cited

U.S. PATENT DOCUMENTS 4,580,568 A 4/1986 Gianturco
5,578,072 A 11/1996 Barone et al.
(Continued)

FOREIGN PATENT DOCUMENTS

EP 0880979 A1 12/1998
EP 1847236 A2 10/2007
(Continued)

OTHER PUBLICATIONS

International Search Report and Written Opinion for Application No. PCT/GB2018/052742 dated Apr. 9, 2020 (9 pages).
(Continued)

*Primary Examiner* — Suzette J Gherbi
(74) *Attorney, Agent, or Firm* — Foley Hoag LLP

(57) ABSTRACT

An endoluminal valve (30) for controlling fluid flow during a surgical procedure is integrated into an access branch (24) of a tubular prosthetic device (10), the access branch (24) receiving a delivery system (100) including a shaft (110), a housing (112) with a depressible finger actuator (122) configured to contact a resilient wall surface (38) of inwardly tapering closure elements (40) of the integrated valve (30), and a fluid venting plug (133) on the shaft (110) which removably seats in an access opening (34) at the proximal end (32) of the endoluminal valve (30), wherein the proximal end (32) is secured within a lumen (26) of the access branch (24) and a distal end (36) of the endoluminal valve (30) located within the lumen (26) comprises self-sealing edges (42) coming together to form a flow-inhibiting seal.

9 Claims, 9 Drawing Sheets

(58) Field of Classification Search
USPC .............................. 623/1.15–1.36, 2.1–2.19
See application file for complete search history.

(56) References Cited

U.S. PATENT DOCUMENTS

| | | | |
|---|---|---|---|
| 6,036,723 A | 3/2000 | Anidjar et al. | |
| 6,773,457 B2* | 8/2004 | Ivancev | A61F 2/07 623/1.28 |
| 7,901,446 B2 | 3/2011 | Fitzpatrick et al. | |
| 8,088,155 B1 | 1/2012 | Lauterjung | |
| 8,088,159 B2 | 1/2012 | Lauterjung | |
| 8,092,511 B2 | 1/2012 | Chuter | |
| 8,486,129 B2 | 7/2013 | Lautherjung | |
| 8,652,195 B2* | 2/2014 | Tani | A61F 2/06 623/1.13 |
| 8,740,971 B2 | 6/2014 | Iannelli | |
| 8,968,389 B2* | 3/2015 | Greenberg | A61F 2/82 623/1.24 |
| 9,398,964 B2 | 7/2016 | McGee et al. | |
| 9,510,936 B2 | 12/2016 | McDonald et al. | |
| 9,622,894 B2 | 4/2017 | McGee | |
| 9,993,329 B2 | 6/2018 | McDonald et al. | |
| 10,137,021 B2 | 11/2018 | McDonald et al. | |
| 10,219,890 B2 | 3/2019 | Madjarov et al. | |
| 10,987,207 B2 | 4/2021 | Wilger et al. | |
| 11,026,823 B2 | 6/2021 | McDonald et al. | |
| 2003/0024527 A1 | 2/2003 | Ginn | |
| 2003/0120263 A1 | 6/2003 | Ouriel et al. | |
| 2003/0130720 A1 | 7/2003 | DePalma et al. | |
| 2004/0117003 A1 | 6/2004 | Ouriel et al. | |
| 2004/0167618 A1 | 8/2004 | Shaolian et al. | |
| 2005/0060029 A1* | 3/2005 | Le | A61F 2/2418 623/2.11 |
| 2005/0075725 A1 | 4/2005 | Rowe | |
| 2005/0137681 A1 | 6/2005 | Shoemaker et al. | |
| 2005/0230956 A1 | 10/2005 | Igeta | |
| 2007/0010873 A1 | 1/2007 | Neri | |
| 2007/0106368 A1 | 5/2007 | Vonderwalde | |
| 2007/0112422 A1* | 5/2007 | Dehdashtian | A61F 2/2433 623/2.11 |
| 2007/0135904 A1 | 6/2007 | Eidenschink et al. | |
| 2007/0168013 A1 | 7/2007 | Douglas | |
| 2008/0082159 A1 | 4/2008 | Tseng et al. | |
| 2008/0147171 A1 | 6/2008 | Ashton et al. | |
| 2009/0264991 A1* | 10/2009 | Paul, Jr. | A61F 2/2418 623/1.35 |
| 2010/0234937 A1 | 9/2010 | Wang et al. | |
| 2011/0190862 A1 | 8/2011 | Bashiri et al. | |
| 2011/0230956 A1 | 9/2011 | White | |
| 2012/0059448 A1 | 3/2012 | Parker et al. | |
| 2012/0071960 A1* | 3/2012 | Tani | A61F 2/07 623/1.15 |
| 2012/0136431 A1 | 5/2012 | Chen | |
| 2012/0158121 A1 | 6/2012 | Ivancev et al. | |
| 2012/0172887 A1 | 7/2012 | Hatfield | |
| 2012/0277849 A1* | 11/2012 | Tani | A61F 2/064 623/1.14 |
| 2013/0131775 A1 | 5/2013 | Hadley et al. | |
| 2013/0166015 A1 | 6/2013 | Roeder | |
| 2013/0218138 A1 | 8/2013 | Fargahi | |
| 2013/0289713 A1 | 10/2013 | Pearson et al. | |
| 2014/0005586 A1 | 1/2014 | Feinstein | |
| 2014/0194970 A1 | 7/2014 | Chobotov | |
| 2014/0200648 A1 | 7/2014 | Newell et al. | |
| 2014/0257452 A1 | 9/2014 | Slazas et al. | |
| 2014/0277332 A1 | 9/2014 | Slazas et al. | |
| 2014/0277345 A1 | 9/2014 | Havel et al. | |
| 2014/0277359 A1 | 9/2014 | Slazas et al. | |
| 2015/0081004 A1 | 3/2015 | Takahashi et al. | |
| 2015/0105819 A1 | 4/2015 | Becking et al. | |
| 2015/0265444 A1 | 9/2015 | Kitaoka | |
| 2019/0192273 A1 | 6/2019 | Debus et al. | |
| 2019/0223996 A1 | 7/2019 | McDonald | |
| 2020/0038169 A1 | 2/2020 | Nelis | |
| 2020/0038184 A1* | 2/2020 | McLean | A61F 2/2436 |
| 2020/0038211 A1 | 2/2020 | Kolbel et al. | |
| 2021/0212846 A1* | 7/2021 | Shahriari | A61F 2/2418 |
| 2021/0228330 A1* | 7/2021 | Kelly | A61F 2/856 |
| 2021/0236257 A1* | 8/2021 | Walzman | A61B 17/32002 |
| 2021/0307641 A1 | 10/2021 | Rumbles et al. | |

FOREIGN PATENT DOCUMENTS

| | | |
|---|---|---|
| EP | 2465471 A2 | 6/2012 |
| EP | 2543342 A1 | 1/2013 |
| EP | 3248572 A1 | 11/2017 |
| JP | H07308330 A | 11/1995 |
| WO | WO-2004/064686 A1 | 8/2004 |
| WO | WO-2006034340 A1 | 3/2006 |
| WO | WO-2008/057569 A1 | 5/2008 |
| WO | WO2008088835 A1 | 7/2008 |
| WO | WO-2008/112270 A1 | 9/2008 |
| WO | WO-2009/009376 A2 | 1/2009 |
| WO | WO-2009/082718 A1 | 7/2009 |
| WO | WO2009129481 | 10/2009 |
| WO | WO2009153768 | 12/2009 |
| WO | WO-2010/053563 A1 | 5/2010 |
| WO | WO-2014096811 A2 | 6/2014 |
| WO | WO-2014/163957 A1 | 10/2014 |
| WO | WO-2016075615 A2 | 5/2016 |
| WO | WO2017136733 | 8/2017 |
| WO | WO-2017/203056 A1 | 11/2017 |
| WO | WO2018060716 A1 | 4/2018 |

OTHER PUBLICATIONS

Search and Examination Report for Application No. GB1715658.9 dated Feb. 28, 2018 (8 pages).

* cited by examiner

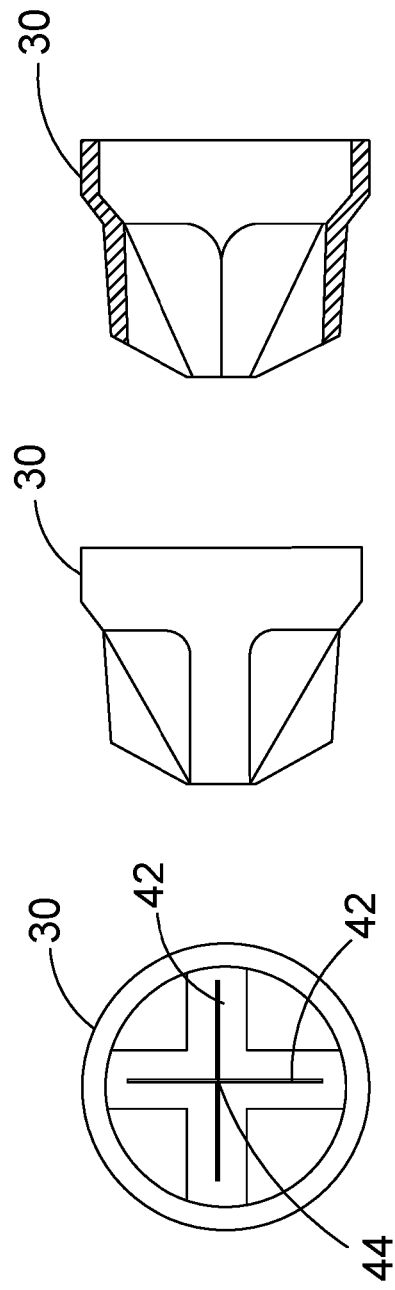
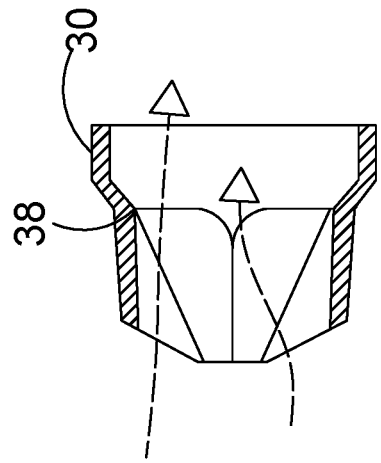
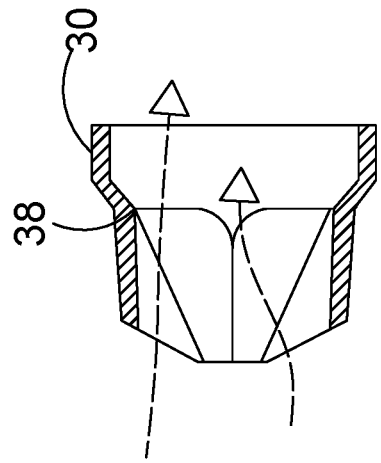
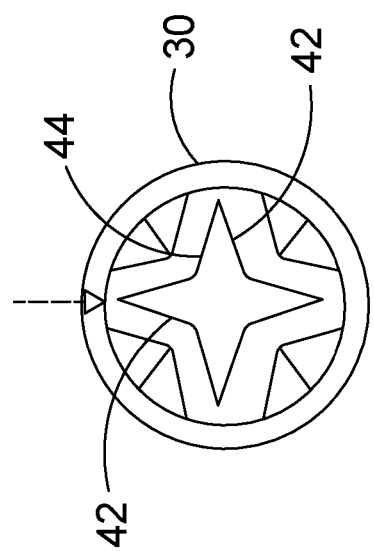
FIG. 3A  FIG. 3B  FIG. 3C  FIG. 3D  FIG. 3E

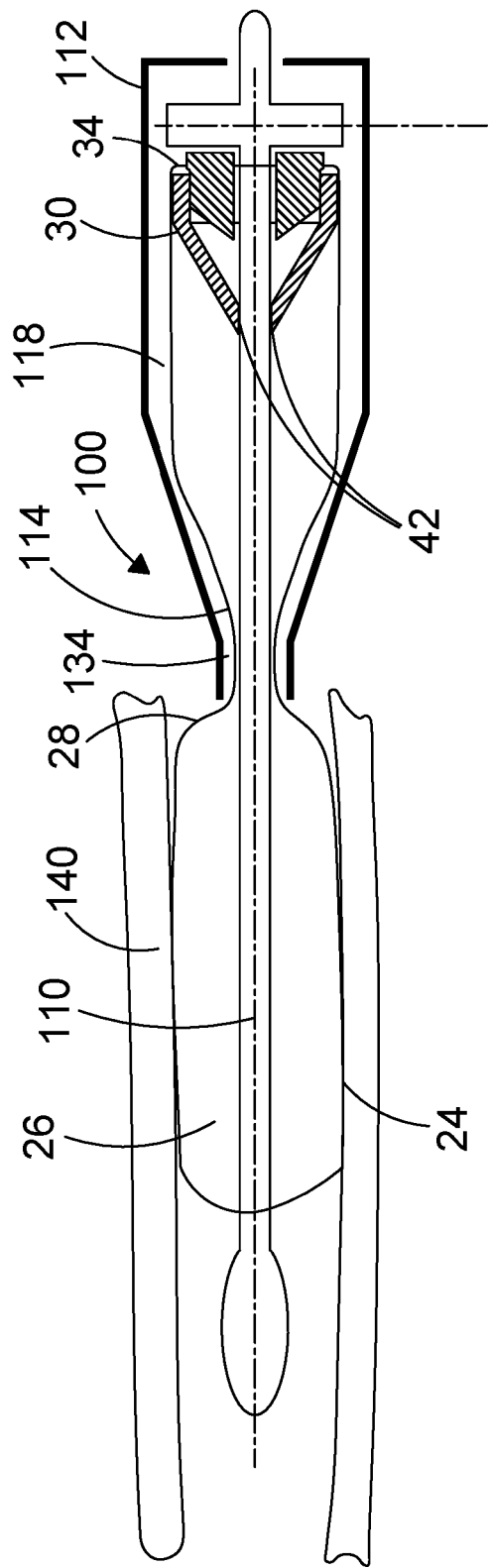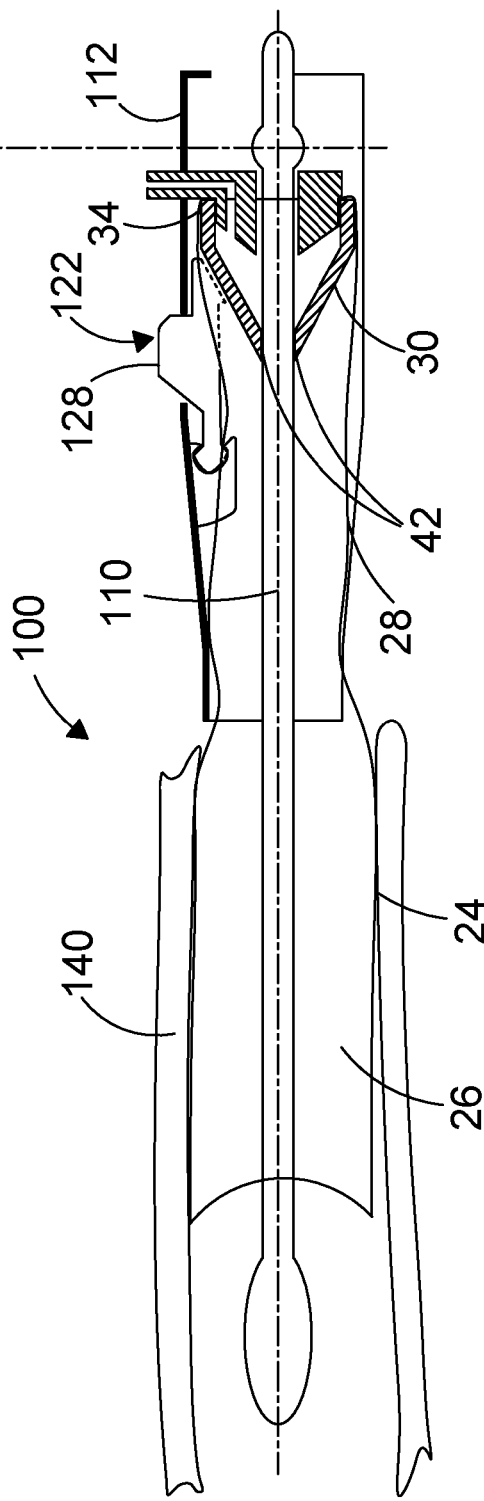
FIG. 4A
FIG. 4B

ENDOLUMINAL DEVICE

FIELD OF INVENTION

A device for use in controlling fluid flow during activities associated with a surgical procedure is disclosed. The device may be used in a delivery system for an endoluminal graft or endoprosthetic device to be delivered in a compact form. The device may be removably incorporated in a lumen of a tubular part of an endoluminal device.

BACKGROUND OF INVENTION

The human body has many tubular organs such as blood vessels, i.e. veins, arteries, intestines, bile ducts, gastrointestinal tract, urinary tract and surgical interventions to repair diseased or damaged tubular organs often involves implanting a tubular graft which may comprise a synthetic fabric construct, or comprise non-native tissue such as porcine tissue (xenograft). The tubular organ may be referred to as a natural vessel herein to distinguish from tubular implants. However, the present disclosure will be made for convenience, without limitation, in the context of repairing tubular organs of the vascular system.

Parts of the vascular system may develop degenerative defects over time, and one such defect is an aneurysm. An aneurysm is an abnormal bulge in the wall of a blood vessel leading to a localised weakening of the blood vessel wall with an increased potential for leakage, rupture and internal bleeding. The aneurysm may cause significant dilation of the natural (native) lumen of the blood vessel compromising natural blood flow.

Conventional methods for treatment of weakened portions of the vasculature include surgical replacement of the affected portion of the aorta, or a more conservative, minimally invasive endovascular repair.

In surgical intervention, the affected part of the blood vessel can be excised and replaced with a prosthetic graft. This invasive approach is normally performed under general anaesthesia with cardiopulmonary by-pass, so that the patient's thorax can be opened and the prosthesis sutured in place of the aneurysmal vessel. Consequently, the method requires the time of a skilled surgeon and prolonged recovery periods for the patient in hospital. Prosthetic grafts normally used for such replacement are typically made from polyester fabric, which may be woven or knitted, and may be sealed with a sealant, for example gelatine or collagen. A tubular graft may include stents of various designs to support the fabric, and may include crimped fabric portions to allow lengthwise axial adjustment and impart some flexibility to allow curved configurations.

The endovascular repair techniques use endoprosthetic devices which are placed within the patient using bespoke delivery systems designed to deliver the endoprosthetic device in a compact "packaged" form for intraluminal delivery, and including removable restraining means, allowing the endoprosthetic device to be delivered, positioned, and finally selectively deployed. When the endoprosthetic device is deployed, the delivery system is removed, allowing the surgical procedure to be completed.

In typical open surgical procedures control of fluid flow, for example to limit blood loss, surgical clamps may be used to temporarily inhibit flow through or from a lumen of one or more natural vessels. The need to cross clamp the device when it is released and removed from the delivery system typically involves more than one person and requires significant and rapid co-ordination to ensure minimum blood loss. Currently to minimise blood loss after the device is removed from the handle, the device is momentarily held closed by the surgeon's fingers while a haemostatic forceps/cross clamp is located and then applied near to the hand held "nipped" fabric.

In a minimally invasive procedure using endoluminal devices in a hybrid surgical technique where a delivery system is used by a surgeon to introduce an endoluminal device, such as a tubular graft, to a surgical site, the use of clamps may be difficult to coordinate sufficiently to minimise blood loss. In such hybrid procedures, the control of fluid flow may involve additional challenges such as venting air from the endoluminal device during the procedure, and controlling blood flow to and around the site for the endoluminal device. The endoluminal device may be an implantable endoprosthetic device to be secured within the lumen of a natural vessel. In the known procedures, the surgeon may be required to use finger pressure to control fluid flow, for example by compressing a part of the endoluminal device during one or more stages of the procedure. It would be desirable to make such a procedure easier for the surgeon.

SUMMARY OF INVENTION

A device for use in controlling fluid flow during a surgical procedure is disclosed. The device may be used in a delivery system including an endoprosthetic device or graft to be delivered endolumenally in a compact form. The device in one aspect comprises an integrated valve located within a lumen of a tubular body forming part of the endoprosthetic device. The device may be integrated into a branch lumen of a tubular body to be delivered endolumenally in a hybrid surgical procedure. The integrated valve may be attached to a fabric part defining the lumen of the tubular body.

The delivery system may comprise a delivery shaft and a handle for a user to manipulate the delivery shaft and control the delivery system, more details of which are to be disclosed hereinafter. The handle for the delivery system may be modified according to another aspect to provide additional fluid flow control during at least part of a procedure. The delivery system may be used in a hybrid surgical procedure.

The use of standard valves in a surgical procedure is known. EP2465471A1 discloses a stent graft device of tubular form, having a temporary bypass branch tube, and a further temporary access branch tube to deliver a covered stent. The temporary access branch tube has a haemoreduction valve mounted at its distal end. Whilst no detail of the valve is disclosed in EP2465471A1, it is believed to be a relatively cumbersome standard valve design including an external side tube comprising a two- or three-way stop cock used for venting air from a system to which the valve is attached. EP2543342A1 discloses an artificial blood vessel provided with an inserting port having a terminal check valve formed from two valve components (dual valve) for passage of a catheter, one valve component being a simple stopper and the other valve component being a "duckbill" check valve permitting through passage of the catheter. The dual valve first valve component preventing fluid loss when the catheter is inserted, and the second (duckbill) valve component preventing fluid loss when the catheter is removed.

In the present disclosure, which is mainly concerned with devices used in an endoluminal aspect of a hybrid surgical procedure, the terms "proximal" and "distal" are used from the perspective of a user of an endoluminal delivery system, so that "proximal" refers a position near to the user, and "distal" refers a position farther from the user. Use of these terms in relation to a device loaded in a delivery system before or during introduction to the lumen of a natural vessel also relies on the orientation of the device with respect to a user, so that "proximal" refers a position near to the user, and "distal" refers a position farther from the user. These terms are used for convenience of discussion and are not intended to limiting. After the device is implanted in an endoluminal location, any convenient point of reference may be used. Typically, a point of conventional reference is the heart of the patient. Thus, with reference to blood vessels, distal would be furthest from the heart. Proximal would be closest. Therefore, attention must be paid to context.

According to an aspect of this disclosure, a "one way" valve for flow control is integrated into a tubular body, especially a branch of a branched tubular body forming part of an endoluminal graft or endoprosthetic device, wherein the valve comprises a valve element having a proximal end within the lumen and secured to a side wall of the branch of the branched tubular body, the proximal end of the valve element including an access opening, the valve element further comprising a distal end located within the branch of the branched tubular body, and the valve element also comprising resilient sidewalls extending from the proximal end towards the distal end, the resilient sidewalls forming closure elements with contact portions coming together at the distal end to form a flow-inhibiting seal.

In embodiments the closure elements with contact portions coming together at the distal end include flat surface contact portions the longest dimension of which may be at least 40% of the axial length of the valve element, preferably more than 50% of the axial length, and preferably in all cases, is less than 95% of the axial length in order to accommodate sufficient space in the access opening for insertion of another component, such as a removable vented plug or hub having a throughbore. The use of flat surface contact portions improves sealing ability of the valve element. The throughbore permits passage of items such as a catheter, shaft, rod, or wire which may form part of, or is used in conjunction with, a delivery system for the endoprosthetic device. In embodiments, the closure elements with contact portions coming together at the distal end meet centrally to form a fluid flow-inhibiting seal.

The presence of the resilient sidewalls means that the sidewalls can be displaced under applied force, for example forced inwardly under finger pressure, or forced apart from a sealing position by pushing through an axially presented item such as a catheter, delivery shaft, rod, or wire, or other elongate tool required for an endoluminal purpose.

The valve element may comprise convergent resilient sidewalls having external surfaces tapering towards the distal end. At least one of said surfaces may be depressible under finger pressure, which pressure may be delivered via an actuator that is external to the valve element.

The access opening at the proximal end of the valve element may sealingly receive a removable vented plug or hub. The removable vented plug or hub conveniently may be mounted upon a delivery shaft of a delivery system for the tubular prosthetic device.

The valve may comprise a plurality, typically three or four, resilient sidewalls having distal leading edges configured to meet to form a central sealable port through which a device or fluid may be forced in the proximal to distal direction. The distal leading edges may meet in cruciform or cross-slit configuration to form a flow-inhibiting seal. When the resilient sidewalls meet to form a central sealable port, flow of fluid back through the valve is resisted due to external fluid pressure on the side walls exceeding fluid pressure on the leading edges forming the central sealable port so that the sidewalls are not likely to be forced open, and the valve performs a non-return function in relation to fluid flow. However an elongate item such as a catheter, or delivery shaft pushed through the valve from the proximal end may be retrieved by pulling back through the central sealable port with sufficient force to displace the distal leading edges of the resilient sidewalls of the valve. After the elongate item is retrieved through the valve, the distal leading edges of the resilient sidewalls of the valve element close up again to maintain a non-return function in relation to fluid flow.

A delivery system for the tubular prosthetic device includes a delivery shaft and a housing attached thereto, the housing serving also as a handle for a user of the delivery system, which housing includes a depressible actuator portion capable of engaging a resilient sidewall of the valve element of the integrated valve within the branch of the tubular prosthetic device when the tubular prosthetic device is located in the delivery system. The housing may have a hollow space for receiving at least a portion of a tubular body. The depressible actuator portion has sufficient depth of travel to contact and move the resilient sidewall and the side wall of the branch of the tubular prosthetic device to which it is secured so that at least a portion of the resilient sidewall and the side wall of the branch of the tubular prosthetic device is also depressed. One effect of the depression of the actuator portion by a user is to create a temporary flow channel through the valve element, which permits venting of fluid, for example air, from inside the tubular prosthetic device via the vented plug mounted upon the delivery shaft of a delivery system for the tubular prosthetic device.

An advantage to a user of the disclosed delivery system of the provision of a depressible actuator portion in the handle of the delivery system is that operation of the valve, for air-venting say, is achievable by a user applying pressure from a single finger without release of the handle of the delivery system such that the user maintains sufficient control of the delivery system whilst actuating the valve.

According to another aspect, the housing is pivotally mounted upon the delivery shaft of the delivery system, and has a lengthwise slot so that the housing can be positioned over and aligned with the delivery shaft for manipulation thereof. The housing may have a hollow space for receiving at least a portion of a tubular body, for example a tubular prosthetic device to be introduced to a lumen of a natural vessel. The hollow space may be accessible via a longitudinally disposed slot in the handle.

The slotted housing may be configured around a delivery shaft upon which a device may be mounted and constrained in a compact form within a removable sheath, the slotted housing forming a removable C-shape clamp valve part about the delivery shaft and compact endoprosthetic device positioned upon the delivery shaft. The pivotal mounting for the housing may be located and spaced distally on the delivery shaft with respect to the position of the C-shape valve part of the housing. The housing being pivotally mounted upon the delivery shaft allows the C-shape clamp valve part to be removed from gripping about the delivery shaft and endoprosthetic device during or after deployment of the endoprosthetic device by removal of a delivery sheath.

Thus when the slotted housing is positioned over the delivery shaft and aligned therewith for use as a handle, it also performs a "nip"-like valve action across a tubular body of a prosthetic device positioned upon the delivery shaft and received in the hollow space of the housing. In this way additional flow control to that obtainable using the valve is available by use of the handle. In an alternative pivoted position, the pivotable slotted housing has been rotated away from its "handle" position over the delivery shaft, and thereby releases the "C"-clamp grip on the tubular body of the prosthetic device. In that alternative position, the housing and the delivery shaft can be readily removed from the tubular body of the prosthetic device. This again is achievable in a single handed action by a user.

In embodiments of the disclosed delivery system, upon user initiated rotation of the housing from its handle position aligned with the delivery shaft, its role as a first stage fluid flow control "C"-clamp device is discontinued and potential blood loss is controlled by the presence of the second stage fluid flow control in the form of the integrated valve. Withdrawal of the delivery system including pull-through of the delivery shaft with its tip through the integrated valve is then achievable, and the pull-through of the delivery shaft also removes the handle from around the branch of the tubular prosthetic device, and removes the vented plug from the access port of the integrated valve. The integrated valve remains secured to a side wall of the branch of the tubular prosthetic device, and self-seals after removal of the delivery system preventing blood loss.

An embodiment of a tubular prosthetic device suitable for endoluminal use comprises
  a tubular main body having a length; and
  an access branch extending laterally from the tubular main body and having a lumen and a side wall, and comprising an integrated valve within the lumen and secured to the side wall, the access branch lumen being in fluid communication with the tubular main body,
  wherein the integrated valve comprises a proximal end within the lumen and secured to a side wall of the access branch of the tubular prosthetic device, the proximal end of the integrated valve including an access opening, the integrated valve further comprising a distal end located within the lumen of the branch of the tubular prosthetic device, the integrated valve also comprising resilient sidewalls extending from the proximal end towards the distal end, the resilient sidewalls forming tapering closure elements with leading edges coming together at the distal end to form a seal.

The integrated valve, as viewed from the distal end may be of a cross-cut or cross-slit configuration, for example a quadricuspid configuration. The said configuration may be formed by the sidewalls comprising substantially V-shaped or L-shaped profile portions as viewed from the distal end. Bicuspid and tricuspid configurations may also be used.

An embodiment of a delivery system suitable for endoluminal use comprises an elongate delivery shaft with a proximal end and a distal end; and a housing pivotally mounted upon the delivery shaft, wherein the housing has a lengthwise slot so that the housing can be positioned over and aligned with the delivery shaft, the housing having a hollow space for receiving at least a portion of a tubular body, and the housing is configured to form a removable C-shape clamp portion positionable to straddle the delivery shaft, and engage with at least a portion of a tubular body. The C-shape clamp portion acts to nip or pinch the portion of the tubular body so that the surgeon does not need to use finger pressure or separate clamping pressure for preventing blood loss at certain stages, such as during deployment of an endoprosthetic device or upon removal of the delivery system.

The elongate delivery shaft may have a vented plug or hub positioned such as to be engageable with an access opening in the valve element of the integrated valve fastened within a lumen of the tubular body of a tubular prosthetic device.

According to another aspect there is provided a delivery system for use with an endoprosthetic device configured for introduction to a lumen of a natural vessel, the system comprising:
  an elongate shaft;
  a housing pivotally mounted upon the shaft, wherein the housing has a longitudinal slot, and a hollow space for receiving at least a portion of a tubular body being part of an endoprosthetic device; and
  an actuator movably attached to the housing and having a contact portion configured to enter the hollow space when depressed by a user of the delivery system.

In embodiments of the delivery system the depressible actuator portion has sufficient depth of travel to contact and move a resilient sidewall of the valve element and the side wall of the branch of the tubular prosthetic device to which it is secured so that at least a portion of the resilient sidewall and the side wall of the branch of the tubular prosthetic device is also depressed sufficiently to create a temporary flow channel through the valve element.

In embodiments the delivery system may comprise an elongate delivery shaft upon which a vented plug or hub is mounted, and the vented plug or hub is insertable into the access opening of the valve element, and removable therefrom when the elongated delivery shaft is withdrawn.

In embodiments of the delivery system, the housing is configured to have a longitudinal slot so that the housing can be positioned over and aligned with the elongate delivery shaft for manipulation thereof, and the housing is pivotally mounted at one end upon the delivery shaft, and the housing is configured at the other end as a C-shape clamp portion positionable to straddle the elongate delivery shaft and engage with at least a portion of the branched tubular body.

In embodiments of the delivery system, the housing has at least portion that is U-shaped, wherein that U-shaped portion has side walls extending from an upper surface opposite to the longitudinal slot to define an internal hollow space for receiving at least a portion of a branched tubular body in which an integrated valve is secured, and one of the side walls has the depressible actuator portion mounted thereon and positioned to engage a resilient sidewall of a valve element of the integrated valve whenever the actuator portion is depressed. The depressible actuator portion may be configured as a tongue or finger with at one end thereof a flexible hinge connection to the side of the U-shaped portion of the housing, and a free end which is moveable by depression through a recess in the side wall to contact the resilient sidewall of the valve element of the integrated valve.

The housing may be made of a medical grade plastics material, such as polyetheretherketone (PEEK).

The various aspects of the devices and systems disclosed herein will now be further described by way of example by reference to the accompanying drawings which for illustrative purposes may omit certain parts from some figures which are largely schematic and not drawn to scale.

BRIEF DESCRIPTION OF THE DRAWINGS

FIG. 3A shows a schematic illustration of a tapered compressible valve element to be integrated into a lumen of an endoluminal graft, the tapered compressible valve element being viewed from the distal end and illustrating a cross-slit seal or "quadricuspid" configuration;

FIG. 3B shows a side view of the tapered compressible valve element illustrated schematically in FIG. 3A, FIG. 3C shows a longitudinal cross-section of the tapered compressible valve element from the side as illustrated schematically in FIG. 3B;

FIG. 3D shows a schematic illustration of the tapered compressible valve element illustrated in FIG. 3A, but illustrating the cross-slit seal in an open configuration;

FIG. 3E shows a longitudinal cross-section of the tapered compressible valve element from the side as illustrated schematically in FIG. 3C, with arrows representing fluid flow through the tapered compressible valve element when at least one surface thereof is depressed;

FIG. 4A shows a schematic illustration of a device comprising an endoluminal graft being deployed in a lumen of natural (native) vessel using a delivery system of FIG. 2B;

FIG. 4B shows schematically a 90° rotated cross-sectional side view of a device comprising an endoluminal graft being deployed in a lumen of natural (native) vessel using a delivery system of FIG. 2B;

DETAILED DESCRIPTION OF THE DRAWINGS

Figure 1:
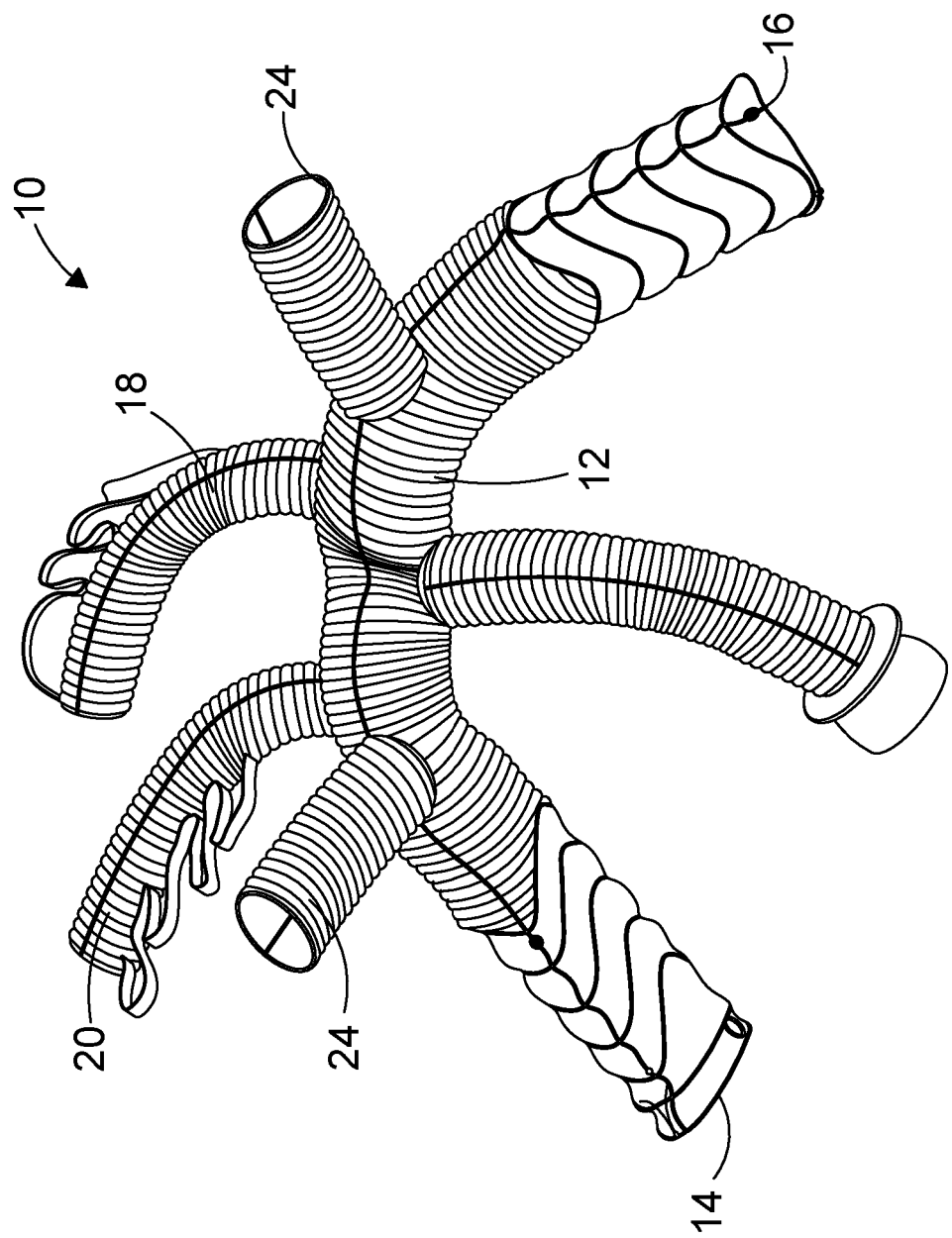
FIG. 1 shows an illustrative example of a branched endoluminal graft with stented portions and unstented crimped portions.

With reference to FIG. 1 there is shown a tubular prosthetic device 10 suitable for endoluminal use. The device 10 comprises a substantially tubular main body 12, which has a length extending from a proximal end 14 of the device to a distal end 16 of the device. The device 10 also comprises first and second branches 18, 20, which are in fluid communication with the main body 12. The device 10 also includes access branches 24. Each of the access branches 24 is in fluid communication with the tubular main body 12, and at least one access branch comprises an integrated valve (not shown in FIG. 1 but described with reference to FIG. 2D below). Each of the access branches 24 may receive a delivery shaft of a delivery system or allow introduction of other items required during the hybrid surgical procedure and is in fluid communication with the tubular main body 12.

Figures 2A, 2B:
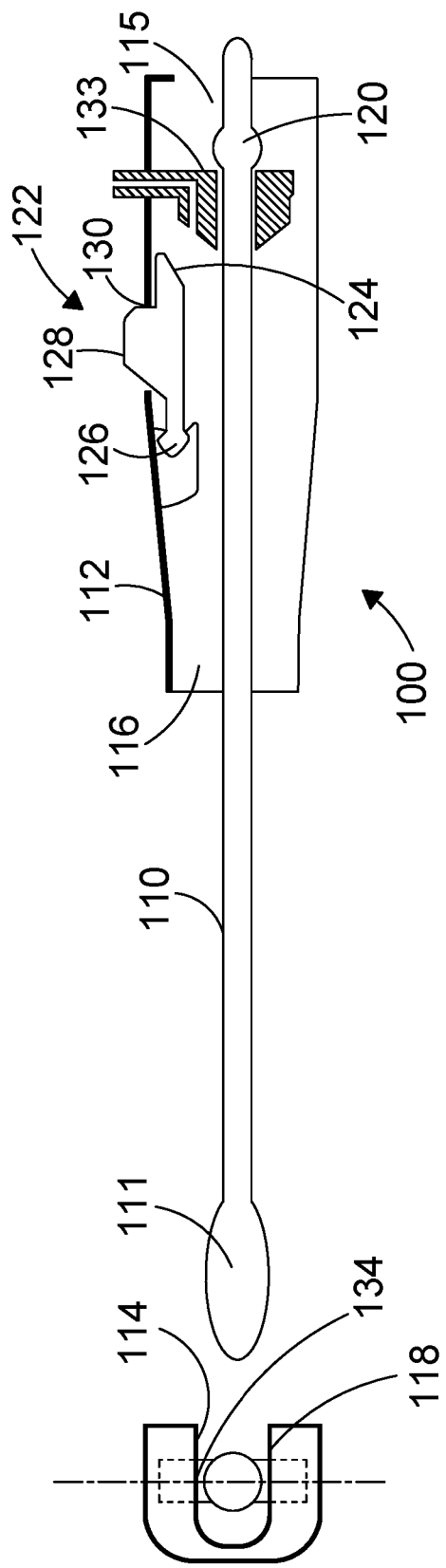
FIG. 2A shows a longitudinal cross-section of a delivery system including a handle and a fluid vent hub with a depressible actuator mounted on the handle, shown here for illustration purposes without any endoprosthetic device loaded therein and without a compressible valve element.
FIG. 2B shows a transverse cross-section of the handle of the delivery system shown in FIG. 2A, and illustrating the C-shaped configuration of the handle.
Figure 2C:
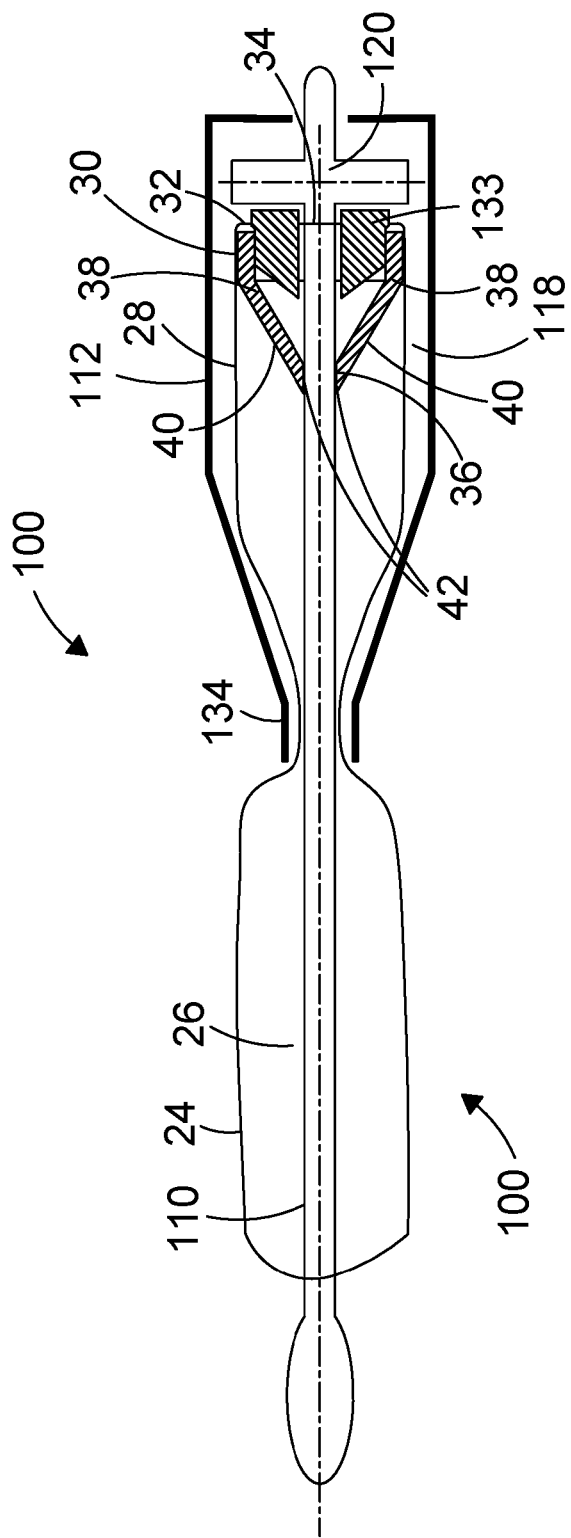
FIG. 2C shows a 90° rotated cross-sectional side view of the delivery system illustrated in FIG. 2A, additionally illustrating a branch portion of an endoluminal graft such as that of FIG. 1 clamped within the handle, the branch portion having an integrated compressible valve element fastened therein and sealingly abutting the fluid vent hub.
Figure 2D:
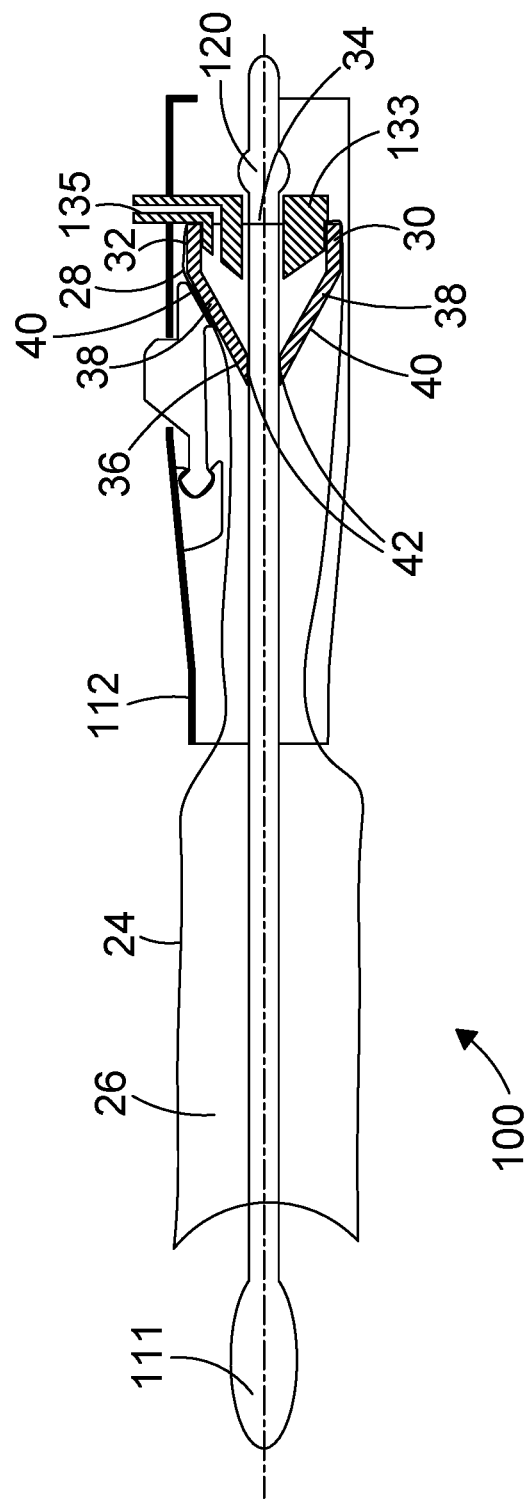
FIG. 2D shows the longitudinal cross-section of the delivery system as shown in FIG. 2A, additionally illustrating a tubular portion of an endoluminal graft such as that of FIG. 1 clamped within the handle, the tubular portion having an integrated compressible valve element fastened therein and sealingly abutting the fluid vent hub, wherein the depressible actuator mounted on the handle is in contact with a surface of the compressible valve element.

Referring now to FIGS. 2A-E, there is shown a delivery system 100 suitable for use with the device 10 described above, which is configured for introduction to a lumen of a natural vessel. The delivery system 100 comprises: an elongate delivery shaft 110 having a tip 111, and a housing 112. The housing 112 is pivotally mounted upon the delivery shaft 110, and comprises a longitudinal slot 114 extending from a proximal end 115 of the housing to a distal end 116 of the housing. The housing 112 also includes a hollow portion 118 of substantially U-shaped cross-section (FIG. 2B) which is suitable for receiving at least a portion of a tubular body being part of an endoprosthetic device, here in this embodiment being the access branch 24 described above. The housing 112 may be pivotally mounted by way of a pivotal mounting 120 located proximate the proximal end 115 of the housing. In the depicted example, the delivery system 100 comprises a vented plug member 133 provided on the delivery shaft 110. The vented plug member 133 is receivable in an access opening 34 of a valve element of the integrated valve 30 of the device 10, as shown in FIG. 2D. In the depicted example, the vented plug member 133 comprises a fluid exit conduit 135.

Figure 2E:
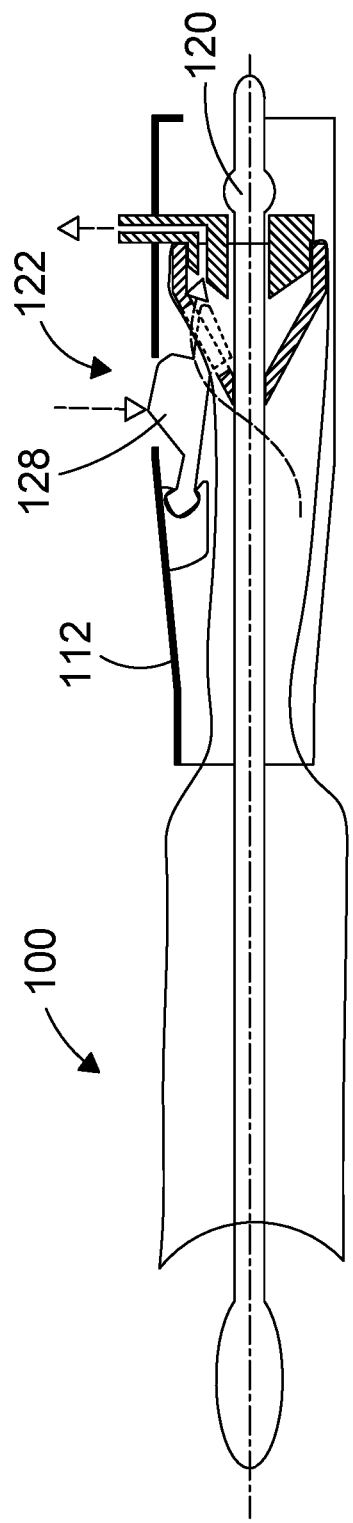
FIG. 2E shows the longitudinal cross-section of the delivery system as shown in FIG. 2C, wherein the depressible actuator mounted on the handle is fully depressed to partially compress the compressible valve element to open a temporary flow channel to allow controlled venting.
Figure 4C:
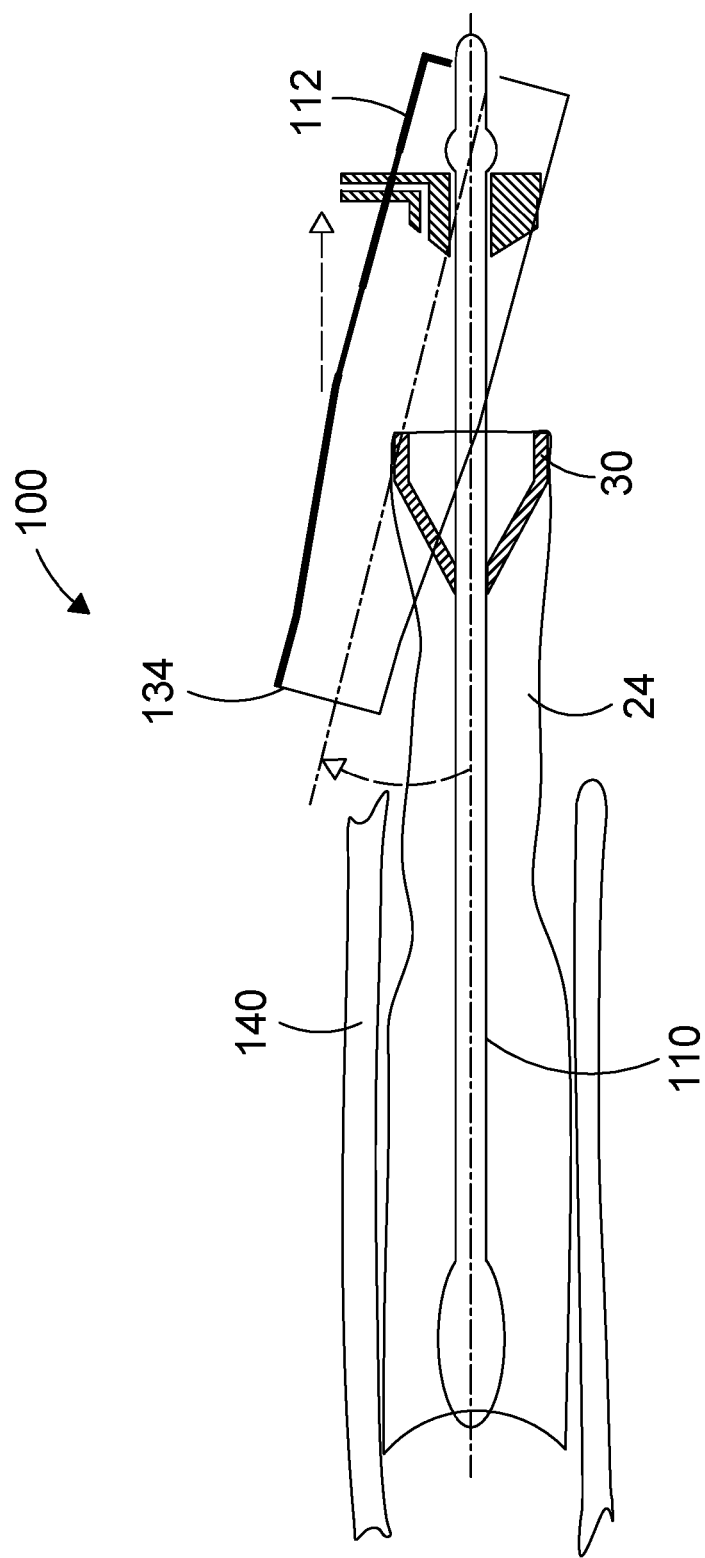
FIG. 4C illustrates schematically a stage in the withdrawal of the delivery system in which a C-shape clamp handle part is pivoted away from a delivery shaft, which shaft is partially withdrawn to disengage the fluid vent hub from the integrated valve element which remains fastened to the fabric of the endoluminal graft.
Figure 4D:
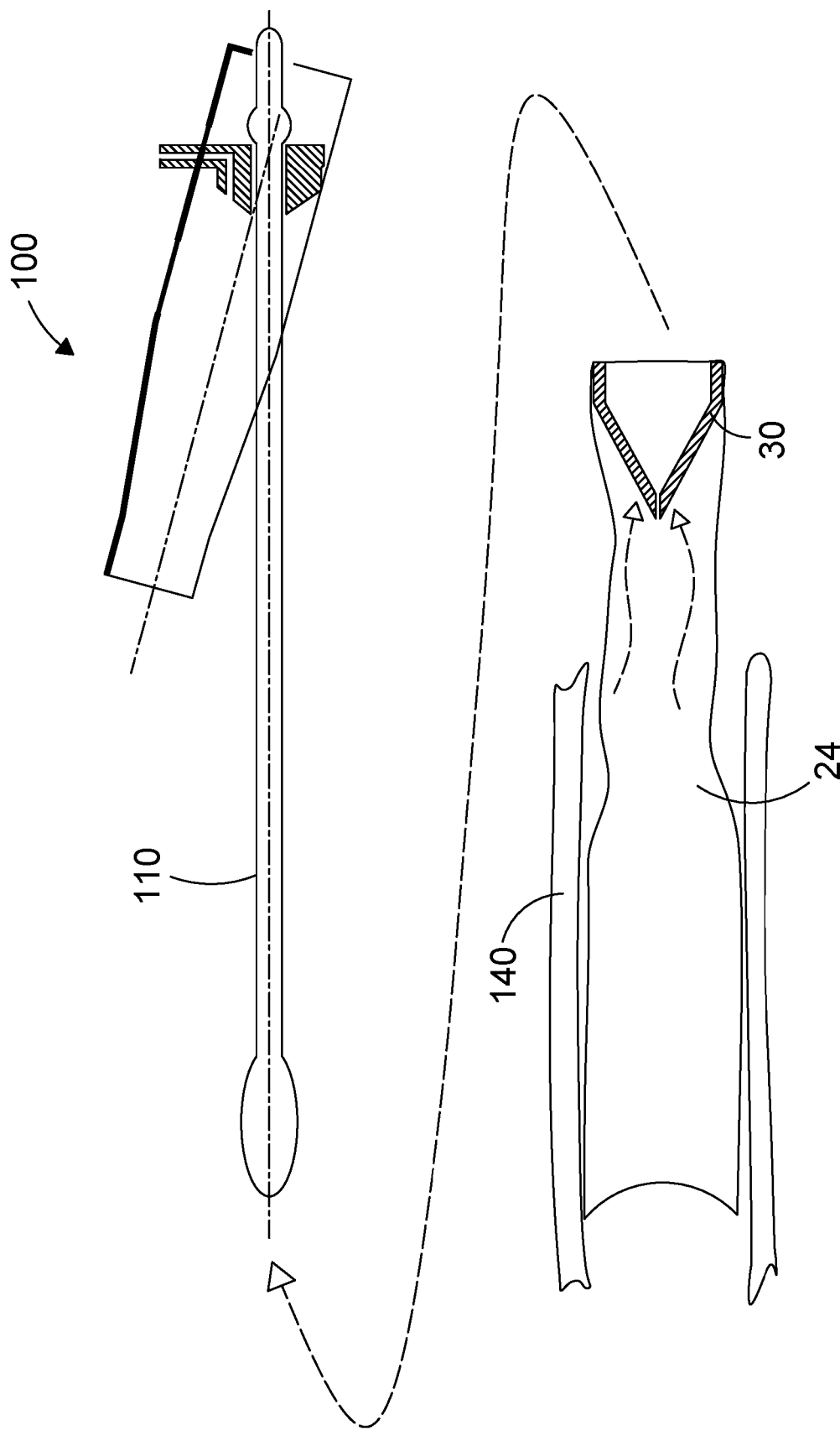
FIG. 4D illustrates schematically a stage in the withdrawal of the delivery system in which the delivery system is removed and the integrated valve element which remains fastened to the fabric of the endoluminal graft provides a closure to obstruct fluid flow out of the endoluminal graft.

The housing 112 also includes a depressible finger actuator 122. The actuator 122 is movably attached to the housing 112, and has a contact portion 124 that is configured to enter the hollow portion 118 when depressed. In the depicted example, the actuator 122 is movably attached to the housing 112 by way of an actuator pivotal mounting 126 located within the housing 112. The actuator 122 also includes a button portion 128 which extends through an actuator aperture 130 provided in the housing 112. The contact portion 124 has a surface which is angled to make contact with a corresponding outer surface portion of the valve element of the integrated valve 30 when depressed by finger pressure applied to the button portion 128 as shown in FIG. 2E.

Referring to FIG. 2D the access branch 24 is depicted with an inserted delivery system 100. The access branch 24 comprises a lumen 26 and a sidewall 28. As shown, the integrated valve 30 is provided within the lumen 26 and includes a resilient tapered valve element secured within the lumen by its proximal end 32 to the sidewall 28 and is provided with an access opening 34. The access opening 34 is configured to receive an elongate shaft of a delivery system upon which is located a vented plug member 133 which removably seats in the access opening 34.

The integrated valve 30 acts as a "one way" valve for flow control.

A distal end 36 of the valve 30 is located within the lumen 26. The valve element of the integrated valve 30 includes a plurality of resilient sidewalls 38, which extend from the proximal end 32 towards the distal end 36 of the integrated valve 30. In different embodiments, three or four such resilient sidewalls 38 cooperate to form inwardly tapering closure elements 40 with leading edges 42 coming together at the distal end 36 to form a flow inhibiting seal. The resilient sidewalls 38 are formed from a compressible biocompatible material such as medical grade silicone rubber.

The integrated valve 30 is configured such that in use, pressure applied against an outer surface of the actuator 122, for example by application of a finger, is transmitted to at least one of the resilient sidewalls 38 causing it to compressibly deform, causing at least one of the leading edges 42 to move away from the others and the seal to break. When the applied pressure is removed, the resilient sidewall(s) 38 recover the original shape, allowing the leading edges 42 to move towards each other and the seal to reform.

The valve element of the integrated valve 30 is shown in greater detail in FIGS. 3A-E. FIG. 3A shows an end view of the valve element of the integrated valve 30 from the distal end 36 in a relaxed uncompressed state. In FIG. 3A no pressure is applied to the outer surface of the resilient side walls 38 of the integrated valve 30. As shown in FIG. 3A, the side walls 38 of the integrated valve 30 meet to form a cruciform slit 44, which may alternatively be described as a "cross-slit". When no pressure is applied to the outer surface of the valve 30 the cross-slit is closed as the leading edges 42 described above are urged towards each other. FIG. 3B shows a side view of the valve element of the integrated valve 30 in the same relaxed state as FIG. 3A, and FIG. 3C shows a longitudinal cross-section of the valve 30 in the same relaxed state as FIG. 3A.

FIG. 3D schematically illustrates pressure being applied to the outer surface of one of the resilient sidewalls 38. As shown, the cross slit 44 is open because the finger pressure causes the resilient sidewalls 38 to deform, meaning the leading edges 42 are caused to move away from each other, which at least partially opens the cross slit 44. FIG. 3E schematically shows direction of fluid flow when the cross slit 44 is open.

Referring to FIGS. 4A to E the use of a C-clamp portion 134 at the free end of the pivotally mounted housing 112 to form a first stage valve to control fluid flow by clamping compression of a portion of the tubular access branch 24 upon the elongate delivery shaft 110 is illustrated.

In use of the delivery system for delivering and deploying a tubular prosthetic device 10, the housing 112 when aligned along the elongate delivery shaft 110 serves as a handle for manipulation of the delivery shaft during a hybrid surgical procedure.

The delivery system would be pre-loaded with a tubular prosthetic device 10 constrained for delivery within a removable sheath as is known in this field.

The surgical field is prepared and the target natural vessel to be repaired is exposed, clamped and surgically opened to allow access for the tubular prosthetic device 10.

During insertion of the tubular prosthetic device 10 de-airing may be accomplished by virtue of the integrated valve 30 and vented plug 133.

After the appropriate surgical steps have been taken to secure the tubular prosthetic device according to the intended procedure, the delivery system may be removed by pivoting the housing 112 to disengage the C-clamp portion 134 from the tubular access branch 24, whereupon the integrated valve 30 inhibits blood loss over the elongate delivery shaft 110 as the elongate delivery shaft is being withdrawn in the next step. The tip 111 of the elongate delivery shaft parts the leading edges 42 of the valve element of the integrated valve 30 which due to resilience close up again after the tip passes through the valve. The access branch 24 can be truncated, sutured and the portion including the integrated valve 30 removed.

SUMMARY

Herein is disclosed an endoprosthetic device and delivery system, wherein an endoluminal valve (30) for controlling fluid flow during a surgical procedure is integrated into an access branch (24) of a tubular prosthetic device (10), the access branch (24) receiving a delivery system (100) including a shaft (110), a housing (112) with a depressible finger actuator (122) configured to contact a resilient wall surface (38) of inwardly tapering closure elements (40) of the integrated valve (30), and a fluid venting plug (133) on the shaft (110) which removably seats in an access opening (34) at the proximal end (32) of the endoluminal valve (30), wherein the proximal end (32) is secured within a lumen (26) of the access branch (24) and a distal end (36) of the endoluminal valve (30) located within the lumen (26) comprises self-sealing edges (42) coming together to form a flow-inhibiting seal.

In particular there is disclosed an endoluminal device for use in a surgical procedure comprising an endoluminal valve (30) integrated into an access branch (24) of a branched tubular prosthetic device (10) comprising a branched tubular body (12), wherein the integrated valve (30) comprises a valve element having a proximal end (32) secured to a side wall of the access branch (24) of the branched tubular body (12), the proximal end (32) of the integrated valve (30) including an access opening (34), the valve element further comprising a distal end (36) located within the access branch (24) of the branched tubular body (12), and the valve element also comprises resilient sidewalls (38) extending from the proximal end (32) towards the distal end (36), the resilient sidewalls (38) forming closure elements (40) with contact portions having self-sealing edges (42) coming together at the distal end (36) to form a flow-inhibiting seal within the access branch (24), the access branch (24) having inserted therein a delivery shaft (110) of a delivery system (100) including a housing (112) with a depressible finger actuator (122) configured to contact a resilient wall surface (38) of the inwardly tapering closure elements (40) of the integrated valve (30), and a fluid venting plug (133) on the shaft (110) which removably seats in the access opening (34) at the proximal end (32) of the endoluminal valve (30), wherein the proximal end (32) is secured within a lumen (26) of the access branch (24).

In embodiments the endoluminal device is provided on a delivery shaft (110) of the delivery system (100) which comprises a tip (111), and a housing (112) having proximal and distal ends (115, 116), the housing (112) being pivotally mounted upon the delivery shaft (110) by way of a pivotal mounting (120) located proximate to the proximal end (115) of the housing, and comprises a longitudinal slot (114) extending from the proximal end (115) of the housing (112) to the distal end (116) of the housing (112) and includes a hollow portion (118) of substantially U-shaped cross-section (FIG. 2B) which is suitable for receiving at least a portion of the tubular body (12), including the access branch (24), the depressible finger actuator (122) being movably attached to the housing (112) by way of an actuator pivotal mounting (126) located within the housing (112) and having a contact portion (124) that is configured to enter the hollow portion (118) through an actuator aperture (130) provided in the housing (112) when a button portion (128) of the depressible finger actuator (122) is depressed.

Provision of an integrated valve located wholly within the lumen is significant in that there can be no external element to interfere with removal of the delivery system (no snagging or entanglement in the limited space of the surgical operating field.

Modifications and improvements may be incorporated without departing from the scope of the invention, which is defined by the appended claims.

The invention claimed is:

1. An endoprosthetic device comprising:
   a) a tubular body that includes a branch having a side wall and defining a lumen; and
   b) an integrated valve located within the lumen, wherein the integrated valve includes
      i) a proximal end defining an access opening,
      ii) a distal end, and
      iii) a valve element having
         a proximal end secured to the side wall of the branch of the tubular body, and
         a distal end located within the branch of the tubular body, the proximal end and the distal end of the valve element defining an axial length of the valve element,
         the valve element including a plurality of resilient sidewalls between the proximal end of the valve element and the distal end of the valve element, the resilient sidewalls being in flat surface contact along at least 40% of the axial length of the valve element.

2. An endoprosthetic device according to claim 1, wherein the valve element further includes convergent resilient sidewalls having external surfaces tapering towards the distal end of the valve element.

3. An endoprosthetic device according to claim 1, wherein the closure elements with contact portions coming together at the distal end have distal leading edges which meet in cruciform or cross-slit configuration to form a flow-inhibiting seal.

4. A delivery system, comprising:
   a) an endoprosthetic device that includes
      i) a tubular body that includes a branch having a side wall and defining a lumen, and
      ii) an integrated valve located within the lumen, wherein the integrated valve includes
         a proximal end defining an access opening,
         a distal end, and
         a valve element having
            a proximal end secured to the side wall of the branch of the tubular body, and
            a distal end located within the branch of the tubular body, the proximal end and the distal end of the valve element defining an axial length of the valve element,
            the valve element including a plurality of resilient sidewalls between the proximal end of the valve element and the distal end of the valve element, the resilient sidewalls being in flat surface contact along at least 40% of the axial length of the valve element;
   c) an elongate delivery shaft;
   d) a vented plug mounted on the elongate delivery shaft and insertable into the access opening; and
   c) a housing that houses at least a portion of the branched tubular body, wherein the housing is attached to the elongate delivery shaft, and including a depressible actuator portion at the resilient sidewalls of the valve element that, upon actuation, creates a flow channel through the valve element branch of a branched tubular body forming part of an endoprosthetic device when by displacing the resilient sidewalls of the valve element and the side wall of the branch of the tubular prosthetic device to which the valve element is secured.

5. A delivery system according to claim 4, wherein the housing defines a longitudinal slot that is aligned with the elongate delivery shaft and the housing is pivotally mounted to the elongate delivery shaft at one end of the delivery shaft, and wherein the housing straddles the elongate delivery shaft and engages at least a portion of the tubular body.

6. An endoluminal device for use in a surgical procedure comprising an endoluminal valve integrated into an access branch of a branched tubular prosthetic device comprising a branched tubular body, wherein the integrated valve comprises a valve element having a proximal end secured to a side wall of the access branch of the branched tubular body, the proximal end of the integrated valve including an access opening, the valve element further comprising a distal end located within the access branch of the branched tubular body, and the valve element also comprises resilient sidewalls extending from the proximal end towards the distal end, the resilient sidewalls forming closure elements with contact portions having self-sealing edges coming together at the distal end to form a flow-inhibiting seal within the access branch, the access branch having inserted therein a delivery shaft of a delivery system including a housing with a depressible finger actuator configured to contact a resilient wall surface of the inwardly tapering closure elements of the integrated valve, and a fluid venting plug on the shaft which removably seats in the access opening at the proximal end of the endoluminal valve, wherein the proximal end is secured within a lumen of the access branch.

7. An endoluminal device according to claim 6, wherein the delivery shaft of the delivery system comprises a tip, and a housing having proximal and distal ends, the housing being pivotally mounted upon the delivery shaft by way of a pivotal mounting located proximate to the proximal end of the housing, and comprises a longitudinal slot extending from the proximal end of the housing to the distal end of the housing and includes a hollow portion of substantially U-shaped cross-section which is suitable for receiving at least a portion of the tubular body, including the access branch, the depressible finger actuator being movably attached to the housing by way of an actuator pivotal mounting located within the housing and having a contact portion that is configured to enter the hollow portion through an actuator aperture provided in the housing when a button portion of the depressible finger actuator is depressed.

8. An endoprosthetic device according to claim 1, wherein the valve element resilient sidewalls define external surfaces that taper toward the distal end of the valve element.

9. An endoprosthetic device according to claim 1, wherein the resilient sidewalls meet in cruciform or cross-slit configuration to thereby form a flow-inhibiting seal.

* * * * *

UNITED STATES PATENT AND TRADEMARK OFFICE
CERTIFICATE OF CORRECTION

PATENT NO. : 11,419,712 B2
APPLICATION NO. : 16/641591
DATED : August 23, 2022
INVENTOR(S) : Gary McDonald It is certified that error appears in the above-identified patent and that said Letters Patent is hereby corrected as shown below:

In the Claims

At Column 11, Lines 60-62, and Column 12, Line 1, Claim number 4:
    c) an elongate delivery shaft;
    d) a vented plug mounted on the elongate delivery shaft and insertable into the access opening; and
    c) a housing that houses at least a portion of the branched
Should read:
    b) an elongate delivery shaft;
    c) a vented plug mounted on the elongate delivery shaft and insertable into the access opening; and
    d) a housing that houses at least a portion of the branched At Column 12, Lines 1-10, Claim number 4:
    c) a housing that houses at least a portion of the branched tubular body, wherein the housing is attached to the elongate delivery shaft, and including a depressible actuator portion at the resilient sidewalls of the valve element that, upon actuation, creates a flow channel through the valve element branch of a branched tubular body forming part of an endoprosthetic device when by displacing the resilient sidewalls of the valve element and the side wall of the branch of the tubular prosthetic device to which the valve element is secured.
Should read:
    c) a housing that houses at least a portion of the branched tubular body, wherein the housing is attached to the elongate delivery shaft, and including a depressible actuator portion at the resilient sidewalls of the valve element that, upon actuation, creates a flow channel through the valve element by displacing the resilient sidewalls of the valve element and the side wall of the branch of the tubular prosthetic device to which the valve element is secured.

Signed and Sealed this
Twenty-fifth Day of October, 2022

*Katherine Kelly Vidal*

Katherine Kelly Vidal
*Director of the United States Patent and Trademark Office*